United States Patent [19]

Tschesche et al.

[11] Patent Number: 6,103,691
[45] Date of Patent: *Aug. 15, 2000

[54] UTILISATION OF ANGIOGENIN AND/OR $\alpha_1$-MICROGLOBULIN AND/OR COMPLEMENT FACTOR D IN ORDER TO INHIBIT THE SECRETION OF PROTEINS

[76] Inventors: Harald Tschesche, Cranachstrasse 18, D-33615 Bielefeld; Ute Hempelmann, Kaasterstrasse 124, D-40670 Meerbusch, both of Germany

[*] Notice: This patent issued on a continued prosecution application filed under 37 CFR 1.53(d), and is subject to the twenty year patent term provisions of 35 U.S.C. 154(a)(2).

[21] Appl. No.: 08/525,716
[22] PCT Filed: Mar. 23, 1994
[86] PCT No.: PCT/DE94/00333
§ 371 Date: Mar. 5, 1996
§ 102(e) Date: Mar. 5, 1996
[87] PCT Pub. No.: WO94/21273
PCT Pub. Date: Sep. 29, 1994
[51] Int. Cl.[7] ............ A61K 38/04; A61K 38/22; A61K 38/36; C07K 14/575; C07K 14/745
[52] U.S. Cl. .............. 514/12; 514/2; 530/324; 530/380
[58] Field of Search ............ 530/300, 350, 530/324, 380; 514/2, 12; 435/69.1

[56] References Cited

FOREIGN PATENT DOCUMENTS 0255011  2/1988  European Pat. Off. .

OTHER PUBLICATIONS

Ngo et al. In: The Protein Folding Problem and Tertiary Structure Prediction Mioz et al (eds.) Birkhauser, Boston, pp. 433, 492–495.
Moore (1994) Trerd. Pharm. Sci 15: 124–129.
Mender (1986) PNAS 83: 1472–1475.

*Primary Examiner*—Jon P. Weber
*Attorney, Agent, or Firm*—Marshall & Melhorn

[57] ABSTRACT

The invention proposes a way to generally prevent or at least severely limit the secretion of proteins, particularly the secretion of enzymes from leucocytes. By administering an agent containing one or more active ingredients selected from the group consisting of angiogenine, $\alpha_1$-microglobulin, complement factor D, fragments or peptides with the biologically effective sequential ranges of these peptides, and peptidomimetica to the source of secretion the secretion can be prevented or at least drastically limited.

17 Claims, 4 Drawing Sheets

Gln-Asp-Asn-Ser-Arg-Tyr-Thr-His-Phe-Leu-Thr-Gln-His-Thr-Asp$^{15}$-Ala-Lys-Pro-Gln-Gly-Arg-Asp-Asp-Arg-Tyr-Cys-Glu-Ser-Ile-Met$^{30}$-Arg-Arg-Arg-Gly-Leu-Thr-Ser-Pro-Cys-Lys-Arg-Ile-Asn-Thr- Phe$^{45}$-Ile-His-Gly-Asn-Lys-Arg-Ser-Ile-Lys-Ala-Ile-Cys-Glu-Asn-Lys$^{60}$-Asn-Gly-Asn-Pro-His-Arg-Glu-Asn-Leu-Arg-Ile-Ser-Lys-Ser-Ser$^{75}$-Phe-Gln-Val-Thr-Thr-Cys-Lys-Leu-His-Gly-Gly-Ser-Pro-Trp-Pro$^{90}$-Pro-Cys-Gln-Tyr-Arg-Ala-Thr-Ala-Gly-Phe-Arg-Asn-Val-Val-Val$^{105}$-Ala-Cys-Glu-Asn-Gly-Leu-Pro-Val-His-Leu-Asp-Gln-Ser-Ile-Phe$^{120}$-Arg-Arg-Pro$^{123}$-Oe

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (iii) HYPOTHETICAL: no (v) FRAGMENT TYPE: internal (ix) FEATURE:
       (A) NAME/KEY: Cross-Links
       (B) LOCATION: 6

(ix) SEQUENCE DESCRIPTION: SEQ ID NO:1:

Gly Leu Thr Ser Pro Cys Lys
1               5

(2) INFORMATION FOR SEQ ID NO:2:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (iii) HYPOTHETICAL: no (v) FRAGMENT TYPE: internal (ix) FEATURE:
       (A) NAME/KEY: Cross-Links
       (B) LOCATION: 10

(ix) SEQUENCE DESCRIPTION: SEQ ID NO:2:

Leu His Gly Gly Ser Pro Trp Pro Pro Cys Glu Tyr Arg
1               5                   10

(2) INFORMATION FOR SEQ ID NO:3:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (iii) HYPOTHETICAL: no (v) FRAGMENT TYPE: internal (ix) SEQUENCE DESCRIPTION: SEQ ID NO:3:

Leu His Gly Gly Ser Pro Trp Pro Pro Ser Glu Tyr Arg
1               5                   10

(2) INFORMATION FOR SEQ ID NO:4:

(i) SEQUENCE CHARACTERISTICS:

-continued

```
        (A) LENGTH: 123 amino acids
        (B) TYPE: amino acid
        (C) STRANDEDNESS: single
        (D) TOPOLOGY: linear (ix) SEQUENCE DESCRIPTION: SEQ ID NO:4:

Gln Asp Asn Ser Arg Tyr Thr His Phe Leu Thr Gln
1               5               10

His Thr Asp Ala Lys Pro Gln Gly Arg Asp Asp Arg
            15              20

Tyr Cys Glu Ser Ile Met Arg Arg Arg Gly Leu Thr
25                  30                  35

Ser Pro Cys Lys Arg Ile Asn Thr Phe Ile His Gly
                40              45

Asn Lys Arg Ser Ile Lys Ala Ile Cys Glu Asn Lys
        50              55              60

Asn Gly Asn Pro His Arg Glu Asn Leu Arg Ile Ser Lys
                65              70

Ser Ser Phe Gln Val Thr Thr Cys Lys Leu His Gly
        75              80              85

Gly Ser Pro Trp Pro Pro Cys Gln Tyr Arg Ala Thr
                90              95

Ala Gly Phe Arg Asn Val Val Val Ala Cys Glu Asn
            100             105

Gly Leu Pro Val His Leu Asp Gln Ser Ile Phe Arg
110                 115             120

Arg Pro
```

UTILISATION OF ANGIOGENIN AND/OR $\alpha_1$-MICROGLOBULIN AND/OR COMPLEMENT FACTOR D IN ORDER TO INHIBIT THE SECRETION OF PROTEINS

FIELD OF THE INVENTION

The invention relates to the utilization, sometimes referred to as utilisation of angiogenin and/or $\alpha_1$-microglobulin and/or complement factor D to inhibit or prevent the secretion of proteins. The invention further relates to a therapeutic agent for the abovementioned utilization, sometimes referred to as utilization.

BACKGROUND OF THE INVENTION

Leucocytes, particularly granulocytes, particularly after stimulation through non-physiological surfaces, by means of chemotaxins such as formylpeptides, complementary components, leucotrienes etc, secrete enzymes, particularly proteases, into their environment. These enzymes (collagenases and gelatinases), serve to enable passage of a cell through the tissue, the removal of destroyed tissue during wound healing, and the decomposition of penetrating foreign bodies. The proteolytic enzymes (collagenase, gelatinase, elastase, cathepsin G and B and others) are normally rapidly inhibited in their local effect by inhibitors (TIMP-1, TIMP-2, a-Proteinase inhibitor, $\alpha_1$-antichymotrypsin, cystatines, $\alpha_1$-macroglobulin and others) of the tissue, serum and blood plasma.

In the case of a massive leucocyte invasion as for example in reactions to inflammations, a condition may arise in which the local inhibitor potential insufficient and the excessive enzyme potential leads to considerable damage to the tissue naturally occurring in the body. Syndromes with such inflammatory derailments are for example emphysema of the lung, inflammatory rheumatoid arthritis, and lupus erythematodes among others. Also, however, haemodialysis in patients with chronic kidney insufficiency leads in the dialyser on the surface of the dialytic membrane to massive activation of the leucocytes with corresponding release of the named enzymes. The same occurs during extra-corporeal circulation in operations (e.g. on the open heart). The enzymes used then lead to considerable (up to 50%) proteolytic destruction of important blood plasma proteins ($\alpha_1$-protease inhibitor, $\alpha_1$-antichymotrypsin, C1-esterase inhibitor among others). Previous therapeutic action in the case of such inflammatory degenerative ailments, e.g. emphysema of the lungs, concentrated on reinstatement of the enzyme/inhibitor balance by therapeutic reinforcement of the inhibitor potential, e.g. infusion of corresponding enzyme inhibitors (Land, H. and Greiling, H. (Hrsg.) Pathobiochemie der Entzündung, Springer verlag, Berlin (1983)).

SUMMARY OF THE INVENTION

Proceeding from this basis, the purpose of the present invention is to indicate known and/or new active ingredients, which will prevent or at least severely limit the secretion of proteins, particularly enzymes, from leucocytes.

Figure 3:
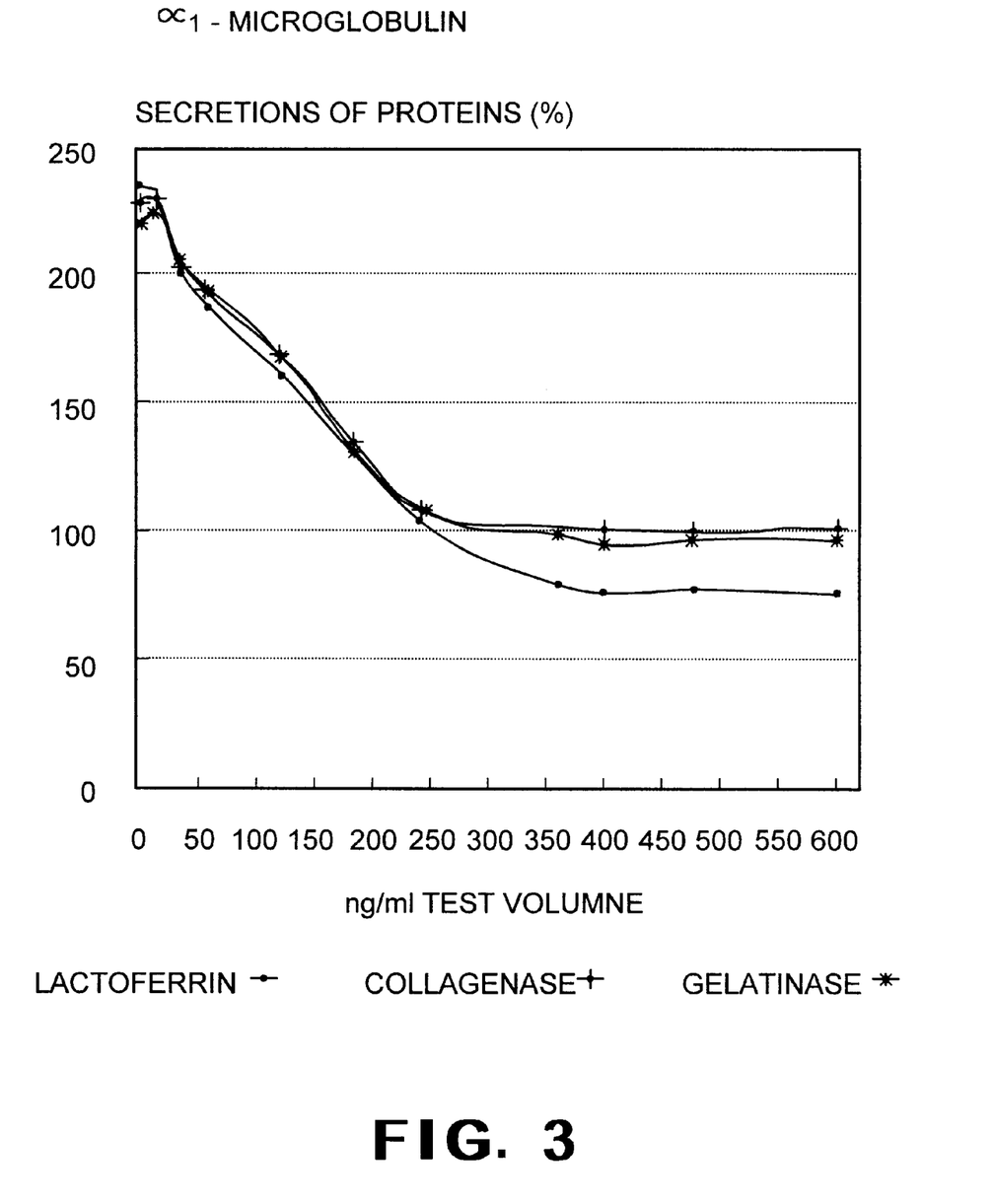
Figure 4:
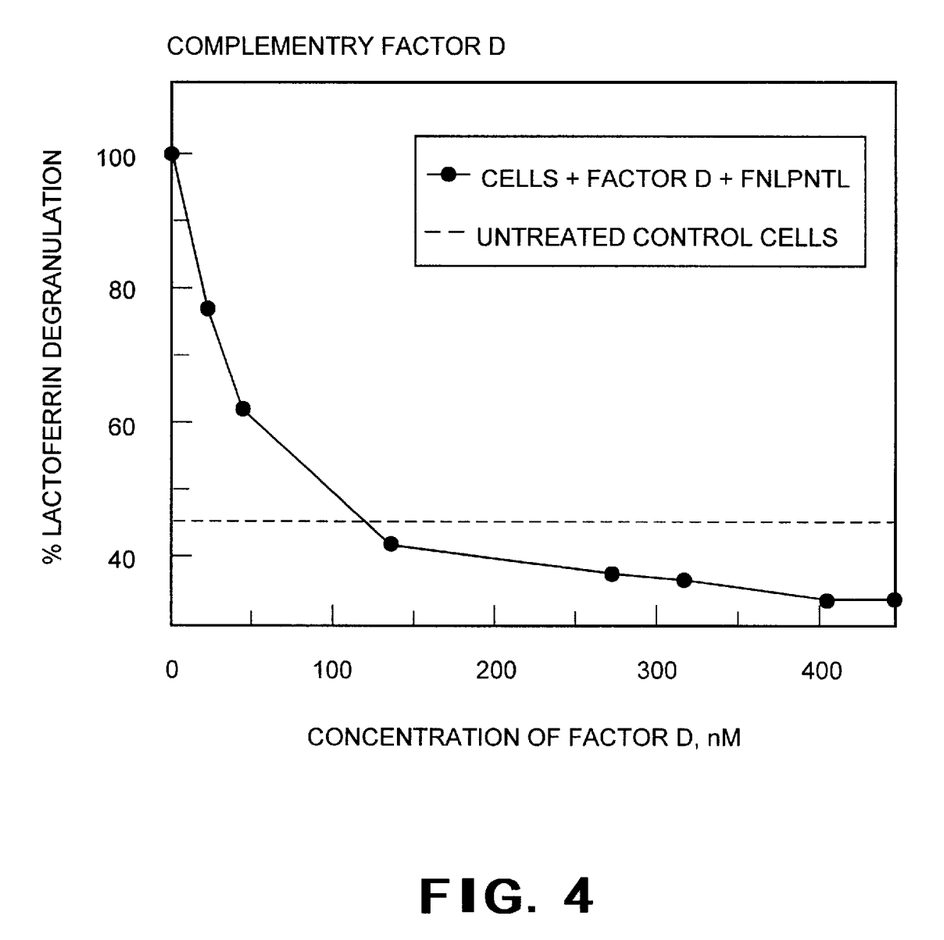

This purpose is fulfilled in that it is firstly proposed, in order to prevent or limit the secretion of proteins, to use materials with a secretion-inhibiting effect. Such materials were firstly discovered as blood plasma proteins, and identified with their novel method of operation. Among these are angiogenin and/or $\alpha_1$microglobulin and/or complement factor D or its fragments, or peptides with the biological effective sequential ranges of these peptides. The protection-inhibiting effect appears particularly clearly in the inhibition curves depicted in FIGS. 2 to 4 for the three proteins. There is simultaneously proposed a new therapeutic agent, as characterised in claims 3 to 8. The secondary claims reveal advantageous further developments.

It was surprisingly discovered that, by means of the use of angiogenin and/or $\alpha_1$-microglobulin, and/or complement factor D and/or its fragments or peptides with the biologically effective sequential ranges of these peptides, the evacuation of the enzymes from the leucocytes is suppressed even in the presence of stimulants. The active ingredients mentioned above are extremely effective in this area and, even in nanomolar concentrations in the medium, suppress the diffusion of proteins inclusive of enzymes from stimulated and unstimulated cells (spontaneous release).

According to the invention, peptidomimetics are understood to be chemical substances whose structure is derived from peptides and in which specific structure areas are replaced by other chemical structures, the biological properties of the original peptide being retained or intensified. Peptidomimetics are for example peptide-similar compounds, in which the peptide bond —CO—NH— is replaced for example by ——CO—CH$_2$—, —CH$_2$, —CH$_2$—, —CH$_2$—NH—, and other groups in which side chains of the natural proteinogenic amino acids are replaced by other chemical structures or compounds in which both is effected, but the biological effect has remained constant.

The Applicant was surprisingly able to show in this respect that the active ingredients mentioned above reveal the utilisation according to the invention both individually and also in combination.

More preferably, it is proposed to use angiogenin and/or its fragments or peptides.

Figure 1:
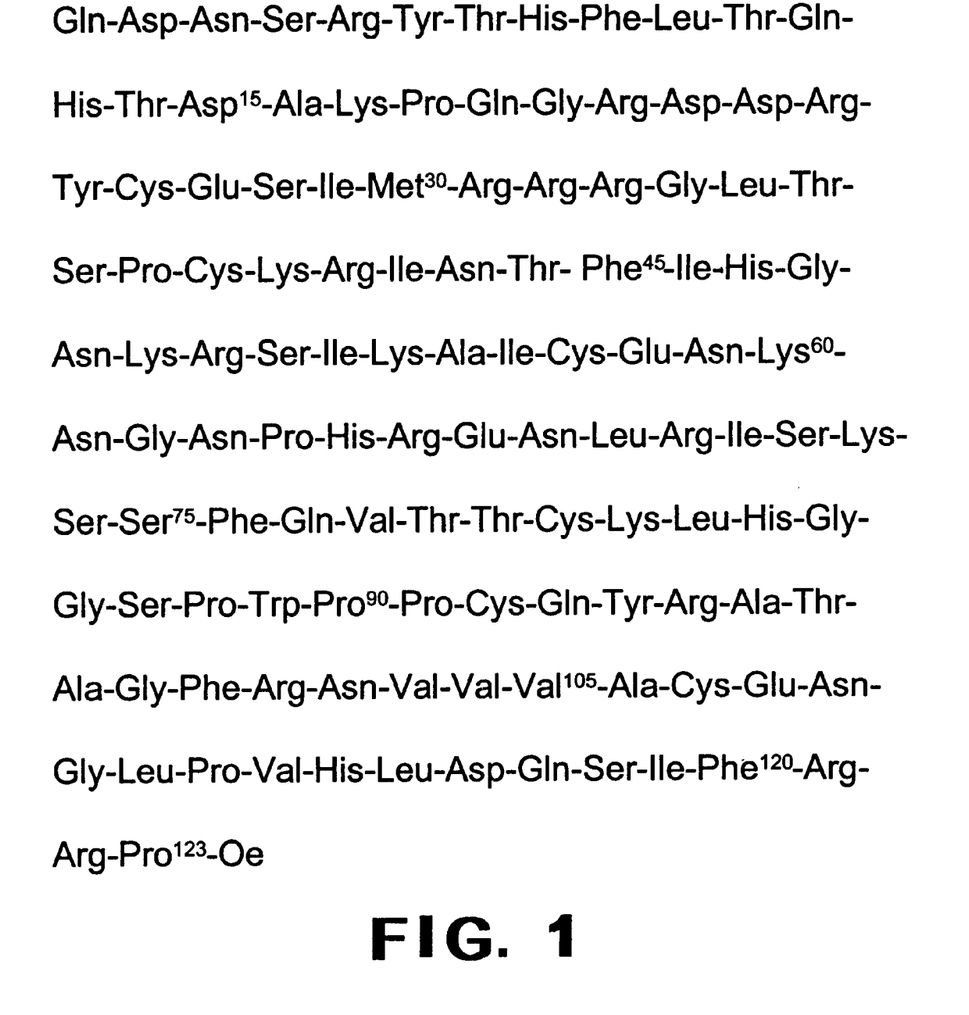
FIG. 1 shows a angiogenin (SEQ ID NO:4) used according to the invention.

It was discovered that, in the use of angiogenin, apart from protein secretion, none of the other anti-inflammatory functions such as chemotaxis, respiratory burst and phagocytosis were lastingly influenced. In this case of the angiogenin used according to the invention (FIG. 1) SEQ ID NO:4, what is involved is human angiogenin with a molecular weight of $M_r$14,400, which occurs as an angiogenetic factor in low concentration in normal human blood plasma (R. Shapiro, D. J. Strydon, K. A. Olson and B. L. Vallee, Biochemistry 26, 5141–5146 (1987)). In terms of molecular weight, immunoreactivity, chromatographic behaviour, amino acid analysis and sequence, the isolated protein is identical with angiogenin. In the degranulation inhibition test on granulocytes, authentic, recombinant angiogenin (K. Kurachi, E. W. Davie, D. J. Strydon, J. F. Riordan and V. L. Vallee, Biochemistry 24, 5494–5499 (1985)) shows the same effect as the isolated protein.

Angiogenin bonds rapidly with the plasma membrane of various cell strains at 37° C. ($t_{1/2}$<1 min), but in comparatively small amounts. It is not a direct mitogen, but it can modulate the primary microgenic stimulation in different cell lines; this correlates with the in-vitro synthesis of phosphatidylinositol, biphosphate, (PtdInsP$_2$). PtdInsP$_2$ has a decisive mediating role in the intracellular signal transduction (W. F. Heath, Jr., F. Moore, R. Bicknell and B. L. Ballee, Proc. Natl. Acad. Sci. USA 86, 2718–2722 (1989)). Angiogenin induces vascularisation in chorioallantoinic membrane of hens and in rabbit cornea (J. W. Fett, D. J. Strydon, R. R. Lobb, E. M. Alderman, H. L. Bethune, J. F. Riordan and B. L. Vallee, Biochemistry 24, 5480–5486 (1985)), and activates the cellular phospholipase C, leading to a temporary rise in intercellular 1, 2-diacylglycerol from the hydrolysis of phosphatidylinositol (R. Bicknell and B. L. Vallee, Proc. Natl. Acad. Sci. USA 85, 5961–5965 (1988)).

Surprisingly, it has become apparent that angiogenin inhibits the spontaneous degranulation of polymorphonucleic leucocytes, (PMNL) by 60% and more. Cells previously incubated with angiogenin no longer react with degranulation to stimulation with FNLPNTL (Formyl-Norleucyl-Leucyl-Phenylalanyl-Norleucyl-Tyrosyl-Leucine). The amount of protein secreted in this case lies 40% below the value for the untreated controls. Multiple washing of these cells with buffer no longer re-establishes the sensitivity to the stimulant FNLPNTL.

The biological activity of degranulation is dependent on concentration. 0.1 µg/ml at least are necessary, in order to cause minimal inhibition of degranulation. No inhibitory effect can be observed below this angiogenin concentration. Maximum inhibition is reached with one µg/ml. An inhibitory effect is however also still achieved at a concentration of 2 µg/ml. Thus the agent must contain the active ingredients in a concentration such that the indicated concentration is achieved in the blood.

The inhibition of degranulation of PMNL is not to be ascribed to destruction of the microtubuli necessary for protein secretion by angiogenin. Even competitive occupation of the FNLPNTL receptors by angiogenin is to be excluded as a cause for the inhibitory effect, as the cells are still capable of chemotaxis along an FNLPNTL gradient.

Angiogenin takes effect within seconds. The cells react to the agent in a time period which is comparable with the reaction to the chemotactic peptide FNLPNTL.

A particularly surprising fact is in particular that, at the named concentrations, angiogenin has no effect on chemotaxis, on phagocytosis and on the "oxidative burst" of PMNL. This is therefore not a general "paralysis" of a cell or of its other biological defensive functions.

The degranulation-inhibiting effect is also achieved by proteolytically-obtained fragments of angiogenin in the same molar concentration. Thus individual isolated tryptic fragments have the same if a slightly reduced effect on granulocytes as the intact angiogenin. In this case there is particularly preferred the fragment with the following sequence, the residues 34–40 being bridged over with the residues 83–95 over Cys:

Also suitable are derivates with a corresponding effect. In this case there is preferred a fragment comprising the amino acid sequence Leu$^{83}$–Arg$^{95}$, with a free Cys at position 92. Similar properties are also obtained with abbreviated sequences, i.e. with sequences in which further amino acids of the chain Leu$^{83}$–Arg$^{95}$ are separated.

The inhibition however is not quite so intense when compared with intact angiogenin.

It is further preferred if the disulphides of the fragments described above are used. The synthetically-produced mixed disulphides in this case show the same effect as the isolated fragment.

However, the invention includes all other fragments insofar as they likewise bring about the inhibition of the secretion of proteins.

The utilisation according to the invention is also achieved by mixtures of complete angiogenin and fragments with the biologically effective sequence ranges. Synthetic peptides are also suitable. These peptides may be present either alone as an active ingredient or in combination with other fragments, or in combination with the complete angiogenin.

Such a synthetic peptide, which likewise has excellent inhibitory properties, contains the residues 83 to 95 with Ser$^{92}$ instead of Cys92. This peptide still possess approximately 50% of the inhibitory effect compared to intact angiogenin. The invention here also includes abbreviated variations thereof.

It is further preferred to use $\alpha_1$-microglobulin. $\alpha_1$-microglobulin is a heterogenically charged clycoprotein with a molecular weight of approximately $M_T$ 30,000 which is excreted in the urine (B. Berggard, B. Ekstrom and B. Akerström, Scand. J. Clin. Lab. Invest. 40, Suppl. 154, 63–71, 1980). Identification was effected via amino acid analysis and analysis of the amino acid sequences. $\alpha_1$-microglobulin is, with 0.03 mg/ml a plasma component, being present at half strength in a 1:1 complex with IgA. (A. Grubb, E. Mendez, J. L. Fernandez-Luna, C. Lopez, E. Mihaesco and J. P. Vaerman, K. Biol. Chem. 261, 14313–14320, 1986). It was also identified in cells of the monocyte-macrophage line in thymus, spleen, lymph nodes, tonsils, hepatocytes and glands of the digestive tract (P. Bonic, C. Vincent and J. P. Revillard, Histochem. J. 16, 1311–1324, 1984). Due to the amino acid sequence, the protein of the lipocalin superfamily of the plasma proteins can be associated (S. Perviaz and K. Brew, Science 228, 335–337 1985)

The immune system is influenced by $\alpha_1$-microglobulin in three ways. The in-vitro stimulation of lymphocytes by various protein antigens is inhibited. This effect is also caused by glycopeptides of the protein, indicating a low significance of the peptide backbone (B. Akerström and L ögdberg, Scand. J. Immunol. 20, 559–563, 1984). $\alpha_1$-microglobulin raises the background incorporation of $^3$H-thymidine in T-cells and B-cells, which is under strict regulation by other serum components (H. Babiker-Mohamed, B. Akerström and L. Lögdberg, Scand. J. Immunol. (in press, 1990)). The in-vitro migration of neutrophile granulocytes is inhibited by $\alpha_1$-microglobulin concentrations above 0.6 mg/ml. (E. Mednez, J. L. Fernandez-Luna, A. Grubb and F. Levya-Cobian, Proc. Natl. Acad. Sci. USA 83, 1472–1475, 1986), but is not influenced by small concentrations. The protein appears to have a physiological function in inflammatory processes which has until now not been clarified.

A receptor for $\alpha_1$-microglobulin has been described on a human cell strain (J. L. Fernandez-Luna, F. Levya-Cobian and F. Mollinedo, FEBS Lett. 2346, 471–474, 1988) which is expressed by addition of PMA to the culture medium.

It has become surprisingly apparent that a$_1$-microglobulin inhibits spontaneous degranulation by 40% and more. If the continuous degranulation is set as equal to 100% as a control value, then the stimulation by FNLPNTL decreases the degranulation to 230%. Cells treated with a$_1$-microglobulin on the other hand show an inhibition of the protein excretion which lies 10–15% below the value of spontaneous degranulation, i.e. at only 85%.

The inhibitor reactivity is dependent on concentration. A minimum inhibition is achieved with 0.1 µg of $a_1$-microglobulin/ml. Lower concentrations cause no appreciable inhibitory effect. Maximum inhibition of degranulation is achievable with 0.2 μg/ml. The inhibition observed is not to be ascribed likewise, to a competitive occupation of the FNLPNTL-receptors by $a_1$-microglobulin, for the reasons already described for angiogenin. It was possible to show that the microtubuli are not destroyed.

The invention also includes biologically active sequence ranges of $\alpha_1$-microglobulin, insofar as they inhibit or or prevent the secretion of proteins.

The Applicant was able to show that, in addition to the two above active ingredients, i.e. angiogenin and $a_1$-microglobulin, complement factor D is also suitable in the same way for the utilisation according to the invention. As already stated it is in this case possible for the individual materials to be used either alone or in combination with one another, or only in combination with individual materials. It has become apparent in this respect that in this case in part additive effects occur, when the normal inhibition has not yet been achieved.

Figure 2:
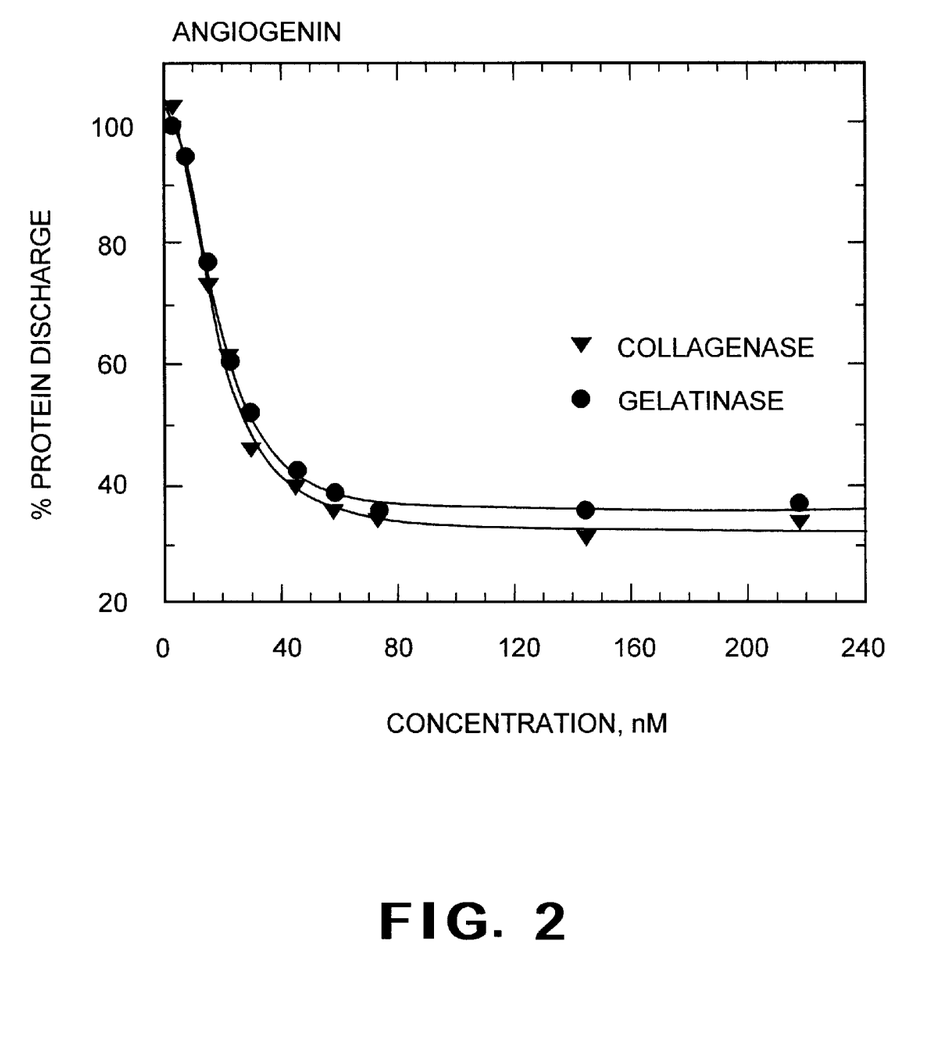
FIGS. 2, 3, and 4 show the protein inhibiting effect of angiogenin, $\alpha_1$-microglobulin, and complement factor D, respectively.

Complementary factor D is identical with human adipsin (White, R. T., Damm, d., Hancock, N., Rosen, B. S., Lowell, B. B., User, P., Flier, J. S. and Spiegelman, B. M. (1992) J. Biol. Chem. 267, 9210–9213). complement factor D has a molecular weight of 24 kD and contains a polypeptide chain. The Applicant was now able to show that complement factor D also inhibits the spontaneous degranulation of polymorphonucleic leucocytes. FIG. 2 shows the effect of complement factor D in the example of lactoferrin degranulation. It was discovered that untreated cells secrete 45% of lactoferrin, whereas the effect visible in FIG. 2 occurs with complement factor D.

The invention further relates to a therapeutic agent for inhibiting or preventing the secretion of proteins. It is proposed according to the invention that the agent contains either $a_1$-microglobulin or complement factor D. It is preferred for the therapeutic agent to contain the above-described active ingredients angiogenin, $a_1$-microglobulin and complement factor D either in combination of all three active ingredients or respectively in a combination of two active ingredients. The therapeutic agent then still conventionally contains the carriers and additives known per se. It is particularly preferred if the therapeutic agent contains the abovementioned fragments of angiogenin.

The agent according to the invention may be administered either in the form of a solution, e.g. for intravenous treatment, as a spray or as a solid formulation.

More preferably, the agent contains the active ingredient in such concentration that a concentration of 0.1 to 2 μg/ml in the blood is achieved. A preferred concentration is 0.8 to 1.2 μg/ml.

For special applications, such for example as for haemodialysis, or in extra-corporeal blood circulation, e.g. by-pass operations, it is preferred to fix the agent on carriers and/or polymers, which then come into contact with the blood, e.g. in containers and apparatus. The agent may also be adsorbed or coupled on lipophile substances, in order in this way to treat surfaces.

It is further preferred to use the agent according to the invention generally for treating inflammatory ailments which are connected with activation of leucocytes.

It is further preferred to use the agent for treatment of septic shock or for early treatment in polytrauma or in order to avoid post-traumatic shock.

DETAILED DESCRIPTION OF THE PREFERRED EMBODIMENTS

The invention is explained in more detail by the following examples:

EXAMPLES 1

Fixation of angiogenin or Angiogenin Peptide.

Methods which are suitable for covalent fixation of proteins and peptides on polymeric carriers, can also serve to couple angiogenin and angiogenin fragments or synthetic peptides or corresponding peptidomimetics on membranes, e.g. dialysis membranes, e.g.:

Agarose Gels

With active carboxyl esters via α- or ε- (amino groups for amide bonding (in accordance with Affigel 10, BioRad Company), With primary amine via Carboxyl group to amide by means of coupling reagent, e.g. water soluble cyclohexyl-carbodiimide (in accordance with Affigel 102) with sulphydryl groups via disulphide bonding to cysteine residues or via thioester (in accordance with Affigel 401)

or

Polyacrylamide Carriers with active hydrazide group via the carboxyl group (according to Hydrazide Biogel P), with primary amine via the carboxyl group (in accordance with Affigel 701)

with Carboxyl group via α- or ε-amino groups by means of coupling reagent, e.g. carbodiimidene or Polystyrol Gels with chlormethyl group to reaction with α- or ε-amino group (according to Bio-Beads SX1)

or

Pericellulose with ONB-carbonate* as reactive group to reaction with α- or ε-amino groups (according to Eurocell ONB-Carbonate of the Company Knauer)

5-Norbornen-2, 3-dicarboxylimidyl-hydrocarbonate esters (CI-CO-ONB)

EXAMPLES 2

Means for inhibiting the degranulation in extra-corporeal circulation.

The agent is dissolved in sterile physiological salt solution, if necessary with the addition of human albumin, and is mixed with the blood stream, so that a maximum concentration of 0.1–1 μg/ml occurs in the circulating blood stream. The maximum requirement per patient thus lies in the order or magnitude of 0.5–5 mg for haemodialysis or extra-corporeal by-pass.

Means for treating lung inflammation

The agent is dissolved in sterile, physiological salt solution (concentration 0.1–1 μg/ml), if necessary supplied with a natural wetting agent, e.g. human, recombinant lung surfactant, and inhaled as an aerosol.

What is claimed is:

1. A method of inhibiting the granular secretion of enzymes from leukocytes, the method comprising administering to the leukocyte a blood plasma protein selected from the group consisting of angiogenin, alpha-1 microglobulin, a synthetic peptide of SEQ ID NO:3, and the disulfide bridged dimeric peptide of SEQ NO. 1 and 2 at a concentration from 0.1 µg/ml to 2 µg/ml.

2. A method as defined in claim 1, in which the blood plasma protein is angiogenin.

3. A method as defined in claim 1, in which the blood plasma protein is alpha-1 microglobulin.

4. A method as defined in claim 1, in which the blood plasma protein is the disulfide bridged dimeric peptide of SEQ NO.1 and 2.

5. A method as defined in claim 1, in which the concentration of the blood plasma protein is about 0.3 to 1.3 µg/ml.

6. A method as defined in claim 1, in which blood plasma proteins are administered comprising angiogenin and alpha-1 microglobulin.

7. A method as defined in claim 1, in which blood plasma proteins are administered comprising angiogenin and the disulfide bridged dimeric peptide of SEQ NO. 1 and 2.

8. A method as defined in claim 1, in which blood plasma proteins are administered comprising the disulfide bridged dimeric peptide of SEQ NO. 1 and 2 and alpha-1 microglobulin.

9. A method as defined in claim 1, in which blood plasma proteins are administered comprising angiogenin and alpha-1 microglobulin and the disulfide bridged dimeric peptide of SEQ NO. 1 and 2.

10. A method as defined in claim 1, in which the blood plasma protein is a bridged peptide of the following sequence:

Gly$^{34}$-Leu-Thr-Ser-Pro-Cys-Lys$^{40}$ (SEQ ID NO:1) Leu$^{83}$-His-Gly-Gly-Ser-Pro-Trp-Pro-Pro-Cys-Glu-Tyr-Arg$^{95}$ (SEQ ID NO:2 ).

11. A method as defined in claim 1, in which the blood plasma protein is a synthetic peptide of the following sequence:

Leu$^{83}$-His-Gly-Gly-Ser-Pro-Trp-Pro-Pro-Ser-Glu-Tyr-Arg$^{95}$ SEQ ID NO:3).

12. A method as defined in claim 1, in which the blood plasma protein is angiogenin consisting of 123-aminoacids, obtained from body fluids or as recombinant protein.

13. A method as defined in claim 1, in which the blood plasma protein is human alpha-1 microglobulin with a median molecular weight of approximately 30,000 obtained from body fluids or recombinant protein.

14. A method as defined in claim 1, in which the blood plasma protein is administered in a concentration in an agent by means of which a maximum concentration results in the blood of about 2 µg/ml.

15. A method as defined in claim 1, in which the blood plasma protein is administered in a corresponding concentration by means of which a maximum concentration in the blood of 0.3 to 1.2 µg/ml results.

16. A method of inhibiting the granular secretion of enzymes from leukocytes, the method comprising administering to the leukocyte a blood plasma protein selected from the group consisting of angiogenin, alpha-1 microglobulin, and the disulfide bridged dimeric peptide of SEQ NO. 1 and 2 at a concentration from 0.1 μg/ml to 2 μg/ml.

17. A method of inhibiting the granular secretion of enzymes from leukocytes in extra-corporeal blood circulation and/or hemodialysis, and/or for treating inflammatory reactions, rheumatoid arthritis, lung emphysema, lupus erythematodes, septic shock and/or polytrauma, the method comprising administering to the leukocyte complement factor D at a concentration from 0.1 μg/ml to 2 μg/ml to a patient in need thereof.

* * * * *